United States Patent
Yoshida et al.

(10) Patent No.: US 10,524,768 B2
(45) Date of Patent: Jan. 7, 2020

(54) MEDICAL IMAGE DIAGNOSTIC APPARATUS AND MEDICAL IMAGE PROCESSING APPARATUS

(71) Applicant: TOSHIBA MEDICAL SYSTEMS CORPORATION, Otawara-Shi (JP)

(72) Inventors: Tetsuya Yoshida, Bergschenhoek (NL); Yoko Okamura, Irvine, CA (US)

(73) Assignee: Canon Medical Systems Corporation, Otawara-shi (JP)

(*) Notice: Subject to any disclaimer, the term of this patent is extended or adjusted under 35 U.S.C. 154(b) by 0 days.

(21) Appl. No.: 14/602,717

(22) Filed: Jan. 22, 2015

(65) Prior Publication Data
US 2015/0201906 A1 Jul. 23, 2015

(30) Foreign Application Priority Data
Jan. 22, 2014 (JP) .................. 2014-009930

(51) Int. Cl.
*A61B 8/08* (2006.01)
*A61B 8/00* (2006.01)
(Continued)

(52) U.S. Cl.
CPC .......... *A61B 8/5207* (2013.01); *A61B 8/0841* (2013.01); *A61B 8/4245* (2013.01);
(Continued)

(58) Field of Classification Search
CPC ..... A61B 8/5207; A61B 8/0841; A61B 8/483; A61B 8/463; A61B 8/466; A61B 17/3403;
(Continued)

(56) References Cited

U.S. PATENT DOCUMENTS

| | | | | |
|---|---|---|---|---|
| 4,459,990 A | * | 7/1984 | Barnea | A61B 6/481 600/431 |
| 6,336,899 B1 | * | 1/2002 | Yamazaki | A61B 8/0833 128/916 |

(Continued)

FOREIGN PATENT DOCUMENTS

| | | |
|---|---|---|
| JP | 2001-218765 | 8/2001 |
| JP | 2011-11001 | 1/2011 |

(Continued)

OTHER PUBLICATIONS

Frank Lindseth, Ultrasound Guided Surgery: Multimodal Visualization and Navigation Accuracy, Norwegian University of Science and Technology, Dec. 2002, Thesis.*
Office Action dated Nov. 28, 2017, in Japanese Patent Application No. 2014-009930 filed Jan. 22, 2014, citing documents AO, AP, and AQ therein. 85 pages.

*Primary Examiner* — Bo Joseph Peng
(74) *Attorney, Agent, or Firm* — Oblon, McClelland, Maier & Neustadt, L.L.P.

(57) ABSTRACT

According to one embodiment, a medical image diagnostic apparatus comprises a position acquisition unit, a data acquisition unit, an alignment unit, a decision unit, and a data generation unit. The position acquisition unit acquires the position of a medical tool in an imaging region with respect to the imaging region at the time of obtaining the medical image. The data acquisition unit acquires volume data corresponding to a three-dimensional region including the imaging region. The alignment unit decides the position of the volume data. The decision unit decides the position of the medical tool with respect to the volume data based on the position of the medical tool and the position of the volume data. The data generation unit generates support volume data by adding support information indicating the position of the medical tool to the volume data.

13 Claims, 5 Drawing Sheets

(51) Int. Cl.
*A61B 17/34* (2006.01)
*A61B 90/00* (2016.01)

(52) U.S. Cl.
CPC .............. *A61B 8/463* (2013.01); *A61B 8/466* (2013.01); *A61B 8/483* (2013.01); *A61B 17/3403* (2013.01); *A61B 8/5261* (2013.01); *A61B 2017/3413* (2013.01); *A61B 2090/364* (2016.02); *A61B 2090/378* (2016.02); *A61B 2090/3762* (2016.02); *A61B 2560/0475* (2013.01)

(58) Field of Classification Search
CPC ............ A61B 8/4245; A61B 2090/378; A61B 2560/0475; A61B 8/5261; A61B 2090/364; A61B 2090/3762; A61B 17/3413; A61B 8/5223; A61B 25/0108; A61B 2017/00106; A61M 25/0108
See application file for complete search history.

(56) References Cited

U.S. PATENT DOCUMENTS

| | | | |
|---|---|---|---|
| 2003/0179915 A1* | 9/2003 | Goto | A61B 6/463 382/128 |
| 2006/0020204 A1* | 1/2006 | Serra | A61B 8/0833 600/437 |
| 2007/0010743 A1* | 1/2007 | Arai | A61B 8/13 600/443 |
| 2008/0019580 A1* | 1/2008 | Ohyu | G06K 9/3216 382/130 |

FOREIGN PATENT DOCUMENTS

| | | |
|---|---|---|
| JP | 2011-251165 | 12/2011 |
| JP | 2012-223500 | 11/2012 |
| JP | 2013-146376 | 8/2013 |

* cited by examiner

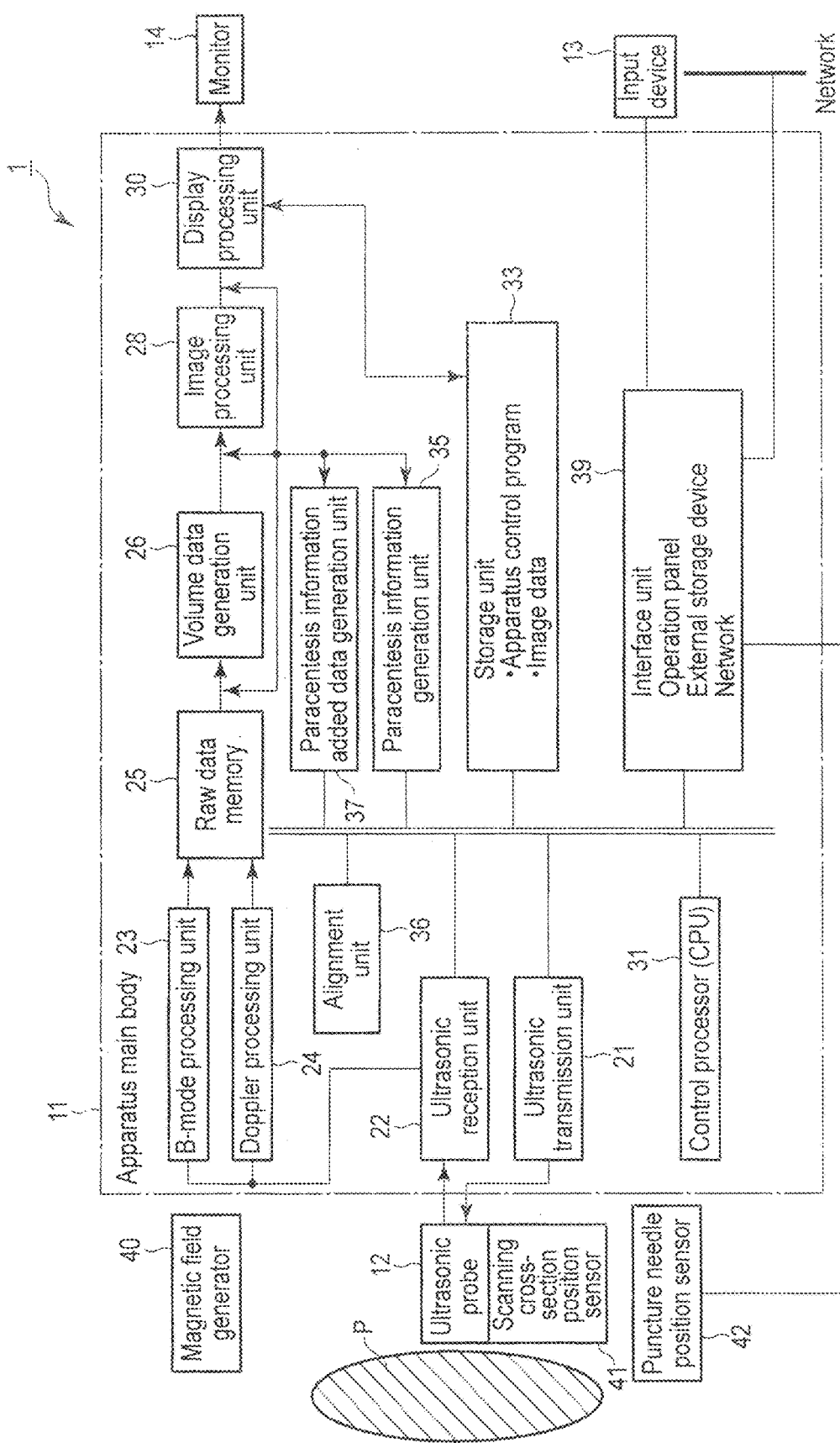
F I G. 1

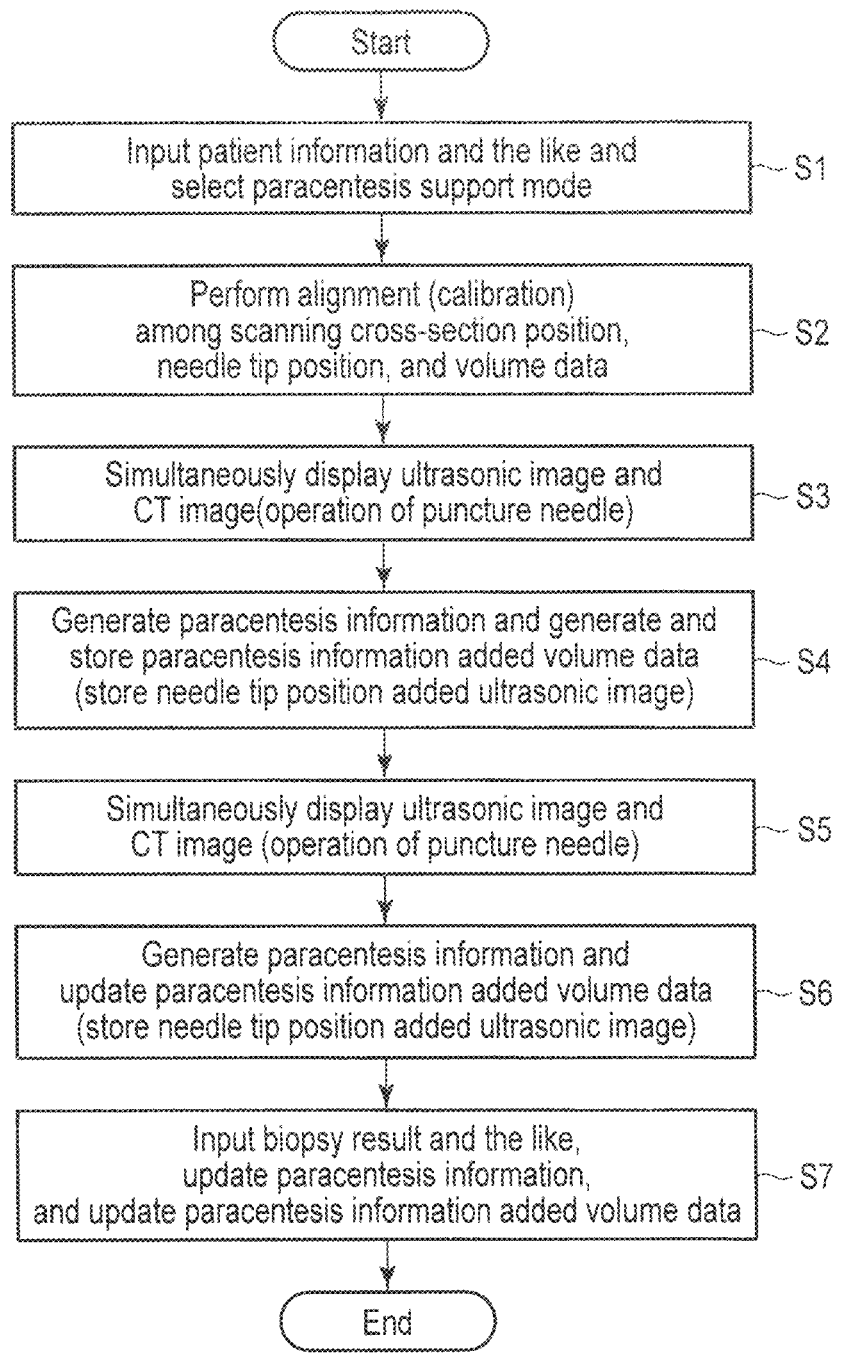
F I G. 2

MEDICAL IMAGE DIAGNOSTIC APPARATUS AND MEDICAL IMAGE PROCESSING APPARATUS

CROSS-REFERENCE TO RELATED APPLICATIONS

This application is based upon and claims the benefit of priority from the prior Japanese Patent Application No. 2014-009930, filed Jan. 22, 2014 the entire contents of which are incorporated herein by reference.

FIELD

Embodiments described herein relate generally to a medical image diagnostic apparatus and a medical image processing apparatus.

BACKGROUND

An embodiment of the present invention relates to a medical image diagnostic apparatus and a medical image processing apparatus which are used for paracentesis.

In the medical field, a medical image of an imaging region in an object (patient) is noninvasively acquired by using a medical image diagnostic apparatus such as an ultrasonic diagnostic apparatus, X-ray computed tomography apparatus, magnetic resonance imaging apparatus, X-ray diagnostic apparatus, or nuclear medicine diagnostic apparatus. For example, ultrasonic diagnosis enables real-time display of how the heart beats or the fetus moves, by simply bringing an ultrasonic probe into contact with the body surface. This technique is also highly safe, and hence allows repeated examination. Furthermore, this system is smaller in size than other diagnostic apparatuses such as X-ray, CT, and MRI apparatuses and can be moved to the bedside to be easily and conveniently used for examination. In addition, ultrasonic diagnosis is free from the influences of exposure using X-rays and the like, and hence can be used in obstetric treatment, treatment at home, and the like.

In general, the frame rate of an ultrasonic diagnostic apparatus is 30 Hz or more. A major feature of this apparatus is that it enables the real-time observation of the dynamic behavior of an organ or blood flow. By using this feature, the ultrasonic diagnostic apparatus is also frequently used for the guidance of a puncture needle. A puncture needle is used for the collection of a tissue sample (biopsy) and has recently been used for paracentesis such as a needle ablation treatment of emitting microwaves or radiowaves from the needle tip. The operator can monitor, in real time, how the needle reaches a treatment region such as a tumor, via an ultrasonic image obtained by using an ultrasonic diagnostic image.

There are several problems in monitoring using ultrasonic images in paracentesis. For example, an ultrasonic diagnostic apparatus is generally designed to acquire two-dimensional tomographic images. For this reason, the range which can be simultaneously visualized in ultrasonic diagnosis is narrower than in an X-ray computed tomography apparatus and a magnetic resonance imaging apparatus. This makes it impossible to accurately record the position of a puncture needle by using a two-dimensional ultrasonic image when the tip of the puncture needle falls outside an ultrasonic scan plane. Recently, an ultrasonic diagnostic apparatus capable of real-time three-dimensional scanning has been developed. This can prevent the needle tip from falling outside a scan volume. Even the use of three-dimensional scanning does not lead to a fundamental solution to problems such as inability to recognize the needle tip position when a high-echo region and the needle overlap.

Under the circumstances, there has recently been proposed a technique of simultaneously displaying, in real time, an ultrasonic tomographic image and a CT tomographic image or MR tomographic image at the same position by attaching a position sensor or the like using magnetism to the probe of an ultrasonic diagnostic apparatus and aligning separately acquired CT volume data (volume data acquired by an X-ray computed tomography apparatus) or MR volume data (volume data acquired by a magnetic resonance imaging apparatus) with the ultrasonic tomographic image. There has also been developed a tool which allows a position sensor to be attached to a needle itself which performs a puncture treatment. Using this tool makes it possible to acquire the relative position between the ultrasonic probe and the needle tip in real time by using the position sensor. In this case, the needle tip can be displayed on an ultrasonic tomographic image while, for example, being highlighted or changed in color tone. These techniques also allow the needle tip position of a puncture needle to be displayed on, for example, CT volume data in real time.

Each conventional apparatus used in paracentesis, however, has a room for improvement from the viewpoint of improving the objectivity of a puncture result, that is, recording the puncture result as an evidence, while sufficiently guaranteeing safety at the time of puncture. For example, strong demands have arisen, in consideration of an improvement in medical quality as well, for the development of an evidence function in a case of inserting a plurality of puncture needles, a function concerning the review of a puncture result, and a function of feeding back a puncture result for effective utilization.

In consideration of the above situation, it is an object to provide a medical image diagnostic apparatus and a medical image processing apparatus which calculate the needle tip position of a puncture needle on volume data used for monitoring at a predetermined timing during paracentesis, store paracentesis information including at least the needle tip position and volume data used for monitoring in association with each other, and can posteriorly reproduce the data.

BRIEF DESCRIPTION OF THE DRAWING

FIG. 1 is a block diagram showing the arrangement of an ultrasonic diagnostic apparatus 1 according to the first embodiment;

FIG. 2 is a flowchart showing a procedure for processing (paracentesis support processing) complying with a paracentesis support function according to this embodiment;

DETAILED DESCRIPTION

Figure 3:
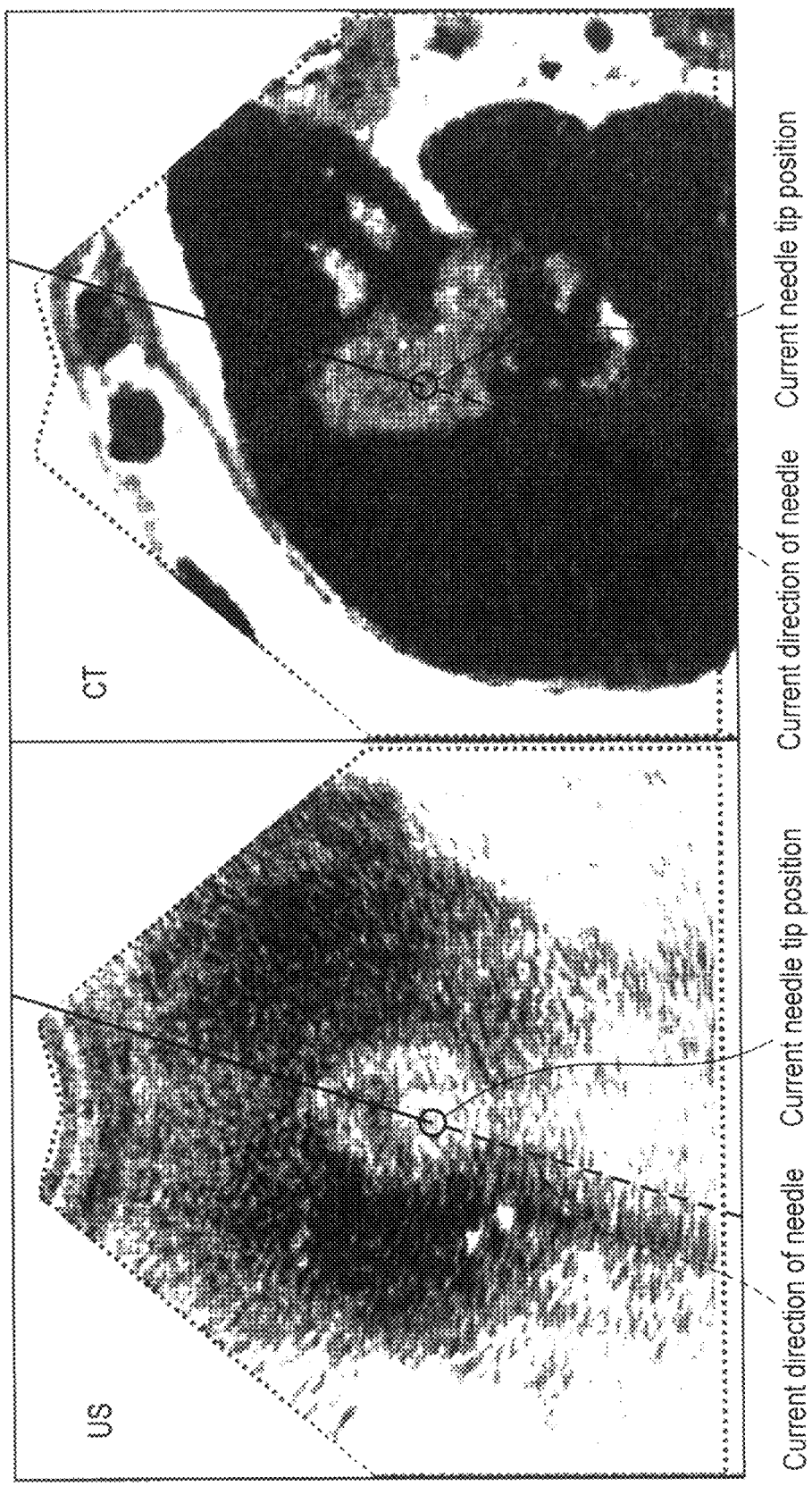
FIG. 3 is a view showing examples of a CT image and an ultrasonic image simultaneously displayed on a monitor 14 by processing in step S3.

In general, according to one embodiment, a medical image diagnostic apparatus comprises an imaging unit, a position acquisition unit, a data acquisition unit, an alignment unit, a decision unit, and a data generation unit. The imaging unit obtains a medical image by using a predetermined region of an object as an imaging region. The position acquisition unit acquires the position of a medical tool in the imaging region with respect to the imaging region at the time of obtaining the medical image. The data acquisition unit acquires volume data corresponding to a three-dimensional region including the imaging region. The alignment unit decides the position of the volume data with respect to the imaging region. The decision unit decides the position of the medical tool with respect to the volume data based on the position of the medical tool with respect to the imaging region and the position of the volume data with respect to the imaging region. The data generation unit generates support volume data by adding support information indicating the position of the medical tool with respect to the volume data to the volume data.

An embodiment will be described below with reference to the accompanying drawing. Note that the same reference numerals in the following description denote constituent elements having almost the same functions and arrangements, and a repetitive description will be made only when required.

FIG. 1 is a block diagram showing the arrangement of an ultrasonic diagnostic apparatus 1 according to this embodiment. As shown in FIG. 1, the ultrasonic diagnostic apparatus 1 includes an ultrasonic probe 12, an input device 13, a monitor 14, an ultrasonic transmission unit 21, an ultrasonic reception unit 22, a B-mode processing unit 23, a Doppler processing unit 24, a raw data memory 25, a volume data generation unit 26, an image processing unit 28, a display processing unit 30, a control processor (CPU) 31, a storage unit 33, a paracentesis information generation unit 35, an alignment unit 36, a paracentesis information added data generation unit 37, and an interface unit 39. A scanning cross-section position sensor 41 and a puncture needle position sensor 42 are connected to the ultrasonic diagnostic apparatus 1. The function of each constituent element will be described below.

The ultrasonic probe 12 is a device (probe) which transmits ultrasonic waves to an object, and receives reflected waves from the object based on the transmitted ultrasonic waves. The ultrasonic probe 12 has, on its distal end, an array of a plurality of piezoelectric transducers, a matching layer, a backing member, and the like. The piezoelectric transducers transmit ultrasonic waves in a desired direction in a scan region based on driving signals from the ultrasonic transmission unit 21, and convert reflected waves from the object into electrical signals. The matching layer is an intermediate layer which is provided for the piezoelectric transducers to make ultrasonic energy efficiently propagate. The backing member prevents ultrasonic waves from propagating backward from the piezoelectric transducers. When the ultrasonic probe 12 transmits an ultrasonic wave to an object P, the transmitted ultrasonic wave is sequentially reflected by a discontinuity surface of acoustic impedance of internal body tissue, and is received as an echo signal by the ultrasonic probe 12. The amplitude of this echo signal depends on an acoustic impedance difference on the discontinuity surface by which the echo signal is reflected. The echo produced when a transmitted ultrasonic pulse is reflected by a moving blood flow is subjected to a frequency shift depending on the velocity component of the moving body in the ultrasonic transmission/reception direction by the Doppler effect.

Note that in this embodiment, the ultrasonic probe 12 is a one-dimensional array probe having a plurality of ultrasonic transducers arrayed along a predetermined direction. However, the present invention is not limited to this. The ultrasonic probe 12 may be a two-dimensional array probe (a probe having a plurality of ultrasonic transducers arrayed in the form of a two-dimensional matrix) or a mechanical 4D probe (a probe which can execute ultrasonic scanning while mechanically swinging an ultrasonic transducer array in a direction perpendicular to the array direction). In addition, it is possible to acquire volume data by performing scanning while moving or swinging a one-dimensional array probe using the scanning cross-section position sensor 41 attached to the probe.

The input device 13 is connected to an apparatus main body 11 and includes various types of switches, buttons, a trackball, a mouse, and a keyboard which are used to input, to the apparatus main body 11, various types of instructions, conditions, an instruction to set a region of interest (ROI), various types of image quality condition setting instructions, and the like from an operator. In addition, the input device 13 includes a button or the like for designating the capturing timing of paracentesis information including the needle tip position of the puncture needle in the paracentesis support function to be described later.

The monitor 14 displays morphological information and blood flow information in the living body as images based on video signals from the display processing unit 30.

The ultrasonic transmission unit 21 includes a trigger generation circuit, delay circuit, and pulser circuit (none of which are shown). The trigger generation circuit repeatedly generates trigger pulses for the formation of transmission ultrasonic waves at a predetermined rate frequency fr Hz (period: 1/fr sec). The delay circuit gives each trigger pulse a delay time necessary to focus an ultrasonic wave into a beam and determine transmission directivity for each channel. The pulser circuit applies a driving pulse to the probe 12 at the timing based on this trigger pulse.

The ultrasonic reception unit 22 includes an amplifier circuit, A/D converter, delay circuit, and adder (none of which are shown). The amplifier circuit amplifies an echo signal received via the probe 12 for each channel. The A/D converter converts each amplified analog echo signal into a digital echo signal. The delay circuit gives the digitally converted echo signals delay times necessary to determine reception directivities and perform reception dynamic focusing. The adder then performs addition processing for the signals. With this addition, a reflection component from a direction corresponding to the reception directivity of the echo signal is enhanced to form a composite beam for ultrasonic transmission/reception in accordance with reception directivity and transmission directivity.

The B-mode processing unit 23 receives an echo signal from the reception unit 22, and performs logarithmic amplification, envelope detection processing, and the like for the signal to generate data whose signal intensity is expressed by a luminance level.

The Doppler processing unit 24 extracts a blood flow signal from the echo signal received from the reception unit 22, and generates blood flow data. In general, the Doppler processing unit 24 extracts a blood flow by CFM (Color Flow Mapping). In this case, the Doppler processing unit 24 analyzes the blood flow signal to obtain blood flow information such as mean velocities, variances, and powers as blood flow data at multiple points.

The raw data memory 25 generates B-mode raw data as B-mode data on three-dimensional ultrasonic scanning lines by using a plurality of B-mode data received from the B-mode processing unit 23. The raw data memory 25 also generates blood flow raw data as blood flow data on three-dimensional ultrasonic scanning lines by using a plurality of blood flow data received from the Doppler processing unit 24. Note that for the purpose of reducing noise or smooth concatenation of images, a three-dimensional filter may be inserted after the raw data memory 25 to perform spatial smoothing.

The volume data generation unit 26 generates B-mode volume data or blood flow volume data by executing raw-voxel conversion including interpolation processing in consideration of spatial position information.

The image processing unit 28 performs predetermined image processing such as volume rendering, MPR (Multi Planar Reconstruction), and MIP (Maximum Intensity Projection) for the volume data received from the volume data generation unit 26. Note that for the purpose of reducing noise or smooth concatenation of images, a two-dimensional filter may be inserted after the image processing unit 28 to perform spatial smoothing.

The display processing unit 30 executes various types of processing associated with a dynamic range, luminance (brightness), contrast, γ curve correction, RGB conversion, and the like for various types of image data generated/processed by the image processing unit 28.

The control processor 31 has the function of an information processing apparatus (computer) and controls the operation of the main body of this ultrasonic diagnostic apparatus. The control processor 31 reads out a dedicated program for implementing the paracentesis support function (to be described later) from the storage unit 33, and loads the program in its own memory, and executes computation, control, and the like associated with each type of processing.

The storage unit 33 stores a dedicated program for implementing the paracentesis support function (to be described later), volume data acquired in the past by other modalities (e.g., an X-ray computed tomography apparatus, magnetic resonance imaging apparatus, and X-ray diagnostic apparatus) or an ultrasonic diagnostic apparatus, diagnosis information (patient ID, findings by doctors, and the like), a diagnostic protocol, transmission/reception conditions, a program for implementing a speckle removal function, a body mark generation program, and a conversion table in which a color data range used for visualization is set for each diagnostic region in advance, and other data groups. The storage unit 33 is also used to archive images in the image memory (not shown), as needed. It is possible to transfer data in the storage unit 33 to an external peripheral device via the interface unit 39.

The paracentesis information generation unit 35 generates information concerning the needle tip position on the current ultrasonic image (i.e., on the current scanning cross-section) based on information concerning the needle tip position of the puncture needle detected by a position detection unit 40. This information can be generated based on, for example, the positional relationship between the needle tip position of the puncture needle and the ultrasonic probe. In addition, the paracentesis information generation unit 35 generates paracentesis information (support information) including the needle tip position on volume data aligned by the alignment unit 36.

The alignment unit 36 performs alignment (calibration) between the current scanning cross-section and volume data (acquired by another modality) used for monitoring.

The paracentesis information added data generation unit 37 generates paracentesis information added volume data by adding the needle tip position information generated by the paracentesis information generation unit 35 to volume data used for monitoring in paracentesis. In addition, the paracentesis information added data generation unit 37 generates and updates paracentesis information added volume data by performing alignment between volume data and newly adding the paracentesis information added to one volume data to the other volume data.

The interface unit 39 is an interface associated with the input device 13, a network, and a new external storage device (not shown). In addition, the interface unit 39 sends out, to the paracentesis information generation unit 35, the scanning cross-section position and the needle tip position of the puncture needle sent out from the scanning cross-section position sensor 41 and the puncture needle position sensor 42. The interface unit 39 can transfer, via a network, data such as ultrasonic images, analysis results, and the like obtained by this apparatus to another apparatus.

A magnetic field generator 40 generates a magnetic field for the calculation of the position of a scanning cross-section by the scanning cross-section position sensor 41 provided on the ultrasonic probe 12 or the calculation of the needle tip position of the puncture needle by the puncture needle position sensor 42 provided on the puncture needle.

The scanning cross-section position sensor 41 is provided at a predetermined position on the ultrasonic probe 12, detects the magnetic field generated by the magnetic field generator 40, and calculates the position of a scanning cross-section based on the detected magnetic field. The calculated position of the scanning cross-section is sent out into the apparatus main body 11 in real time via the interface unit 39.

The puncture needle position sensor 42 is provided on the needle tip or proximal end of the puncture needle, a puncture needle adapter which always maintains a predetermined relative positional relationship with the puncture needle, or the like, detects the magnetic field generated by the magnetic field generator 40, and calculates the needle tip position of the puncture needle based on the detected magnetic field. Note that when attaching the puncture needle position sensor 42 to the proximal end of the needle, it is necessary to perform calibration between the puncture needle position sensor 42 and the needle tip position in advance. The calculated needle tip position of the puncture needle is sent out in real time into the apparatus main body 11 via the interface unit 39. A plurality of puncture needle position sensors 42 may be attached to the puncture needle. For example, it is possible to detect the three-dimensional direction (tilt) of the puncture needle by attaching puncture needle position sensors at two positions, namely the tip and proximal end of the puncture needle and making each sensor detect position information.

(Paracentesis Support Function)

The paracentesis support function of this ultrasonic diagnostic apparatus will be described next. This function calculates the needle tip position of the puncture needle on volume data used for monitoring at a predetermined timing during paracentesis, stores paracentesis information including at least the needle tip position and the volume data used for monitoring in association with each other, and enables visual recognition of the position of the puncture needle on the volume data at the predetermined timing during or after the paracentesis, as needed.

FIG. 2 is a flowchart showing a procedure for processing (paracentesis support processing) complying with this paracentesis support function. The contents of processing executed in each step in paracentesis support processing will be described with reference to FIG. 2.

[Input of Patient Information and the Like/Selection of Paracentesis Support Mode and Volume Data: Step S1]

The operator executes, via the input device 13, input of patient information, examination information, and the like, selection of a paracentesis support mode of executing this paracentesis support function, and selection of predetermined volume data used for monitoring in paracentesis (step S1). The storage unit 33 automatically stores the input and selected various types of information. In addition, the control processor 31 activates a program for executing the paracentesis support function and reads out the selected volume data from the storage unit 33 in response to the selecting operation for the paracentesis support mode.

For the sake of a concrete description, assume that in this embodiment, the volume data selected by the operator is that acquired by an X-ray computed tomography apparatus. However, the present invention is not limited to this, and the selected volume data may be that acquired by a magnetic resonance imaging apparatus, X-ray diagnostic apparatus, ultrasonic diagnostic apparatus, or the like.

[Association Among Ultrasonic Probe Position, Needle Tip Position, and Volume Data Position: Step S2]

The alignment unit 36 then executes association (calibration) among the volume data selected by the operator, the scanning cross-section position received from the scanning cross-section position sensor 41, and the needle tip position received from the puncture needle position sensor 42 (step S2).

[Simultaneous Display of Ultrasonic Image/CT Image: Step S3]

The control processor 31 then generates a CT image corresponding to the current scanning cross-section by using the scanning cross-section position received from the scanning cross-section position sensor 41 and the volume data having undergone alignment processing. The control processor 31 also generates an ultrasonic image concerning the current scanning cross-section acquired by normal processing. The monitor 14 simultaneously displays an ultrasonic image and a CT image which correspond to the generated current scanning cross-section in a predetermined form (step S3). Note that the CT image and the ultrasonic image which are simultaneously displayed in this manner are updated in real time every time a new scanning cross-section position is received from the scanning cross-section position sensor 41.

FIG. 3 shows examples of a CT image and an ultrasonic image which are simultaneously displayed on the monitor 14 by the processing in this step. As shown in FIG. 3, the operator can operate the puncture needle while visually recognizing the current position and direction of the puncture needle easily and quickly using both the CT image and the ultrasonic image which are simultaneously displayed.

[Generation of Paracentesis Information and Storage of Paracentesis Information Added Volume Data: Step S4]

The paracentesis information added data generation unit 37 then generates paracentesis information including at least a needle tip position on volume data by using the needle tip position received from the puncture needle position sensor 42 in response to a predetermined event as a trigger. In addition, the paracentesis information added data generation unit 37 generates paracentesis information added volume data by adding the above paracentesis information to the volume data and stores the generated data in the storage unit 33. At the same time, the control processor 31 calculates a needle tip position on the ultrasonic image by using the needle tip position received from the puncture needle position sensor 42, and stores the ultrasonic image to which the needle tip position is added in the storage unit 33 in association with the paracentesis information added volume data (step S4).

Note that the above trigger event in step S4 is not specifically limited. Typically, it is possible to use, as a trigger event, a generate/store instruction for paracentesis information added volume data input from the input device 13 at a desired timing, a freeze display instruction or store instruction for an ultrasonic image input from the input device 13 at a desired timing, or the like. Alternatively, from a clinical viewpoint, it is possible to use, as a trigger event, a cauterization start instruction if paracentesis is RFA, a tissue collection start operation if paracentesis is biopsy (tissue collection), or the like. When performing tissue collection by using a gun-type puncture needle, the needle tip instantaneously extends and contracts. It is difficult for the operator to press a switch in accordance with the movement of the needle. It is possible to store a needle tip position and ultrasonic image data at the exact timing of tissue collection by automatically storing the data when the direction of the needle tip is inverted by 180° after the operator presses the switch and the velocity of the needle tip exceeds a threshold. Alternatively, it is possible to set, as the point of the occurrence of a trigger event, the point at which an arbitrary time has elapsed since the operator pressed the switch. In addition, as paracentesis information added volume data and an ultrasonic image to which a needle tip position is added, not only those corresponding to a given time but also, for example, those over a period before and after cauterization or those over a period before and after tissue collection may be automatically generated and stored in chronological order. Alternatively, it is possible to set, as the point of the occurrence of a trigger event, the point at which a predetermined time has elapsed since the insertion of the puncture needle into a tissue, with time point at which the puncture needle has remained still for a predetermined time being regarded as the timing of the execution of paracentesis.

In addition, the paracentesis information generated by the paracentesis information added data generation unit 37 can include various types of information, as needed. Typically, such information includes the date and time of the occurrence of the above trigger event, an operation type, an operator, the thickness of a puncture needle, a place, and operator's comments.

[Simultaneous Display of Ultrasonic Image/CT Image, Updating of Paracentesis Information Added Volume Data, and the Like: Steps S5 and S6]

The current scanning cross-section position is updated in real time every time a new one is received from the scanning cross-section position sensor 41. The operator continuously operates the puncture needle while observing a CT image and an ultrasonic image which are continuously and simultaneously displayed (step S5).

Subsequently, in paracentesis, the paracentesis information added data generation unit 37 generates paracentesis information including at least information for indicating the needle tip position on volume data by using the needle tip position received from the puncture needle position sensor 42 in response to a new event as a trigger as in step S4. In addition, the paracentesis information added data generation unit 37 updates the stored paracentesis information added volume data by adding newly generated paracentesis information to the volume data while leaving the paracentesis information generated in step S4 unchanged (differentiating the paracentesis information generated in step S4). At the same time, the control processor 31 stores an ultrasonic image to which the needle tip position on the ultrasonic image, calculated by using the needle tip position received from the puncture needle position sensor 42, is added, in the storage unit 33 in association with the paracentesis information added volume data (step S6).

Note that the processing in steps S5 and S6 is repeatedly executed as needed during paracentesis. [Input of Biopsy Results and The Like, Updating of Paracentesis Information Added Volume Data, and The Like: Step S7]

A biopsy result and the like are input from the input device 13 as needed. The paracentesis information added data generation unit 37 updates paracentesis information corresponding to the position of the biopsy site so as to include the input biopsy result and the like. In addition, the paracentesis information added data generation unit 37 updates the stored paracentesis information added volume data by adding the paracentesis information updated so as to include the biopsy result and the like to the volume data while leaving the previously generated paracentesis information unchanged (step S7).

(First Application)

It is possible to reproduce paracentesis information added volume data stored at an arbitrary timing after examination. That is, the control processor 31 reads out the paracentesis information added volume data stored in the storage unit 33 in response to a reproduction instruction input from the input device 13, generates, for example, a CT image (MPR image or the like) used for monitoring in paracentesis, and displays the image together with the paracentesis information on the monitor 14.

Figure 4:
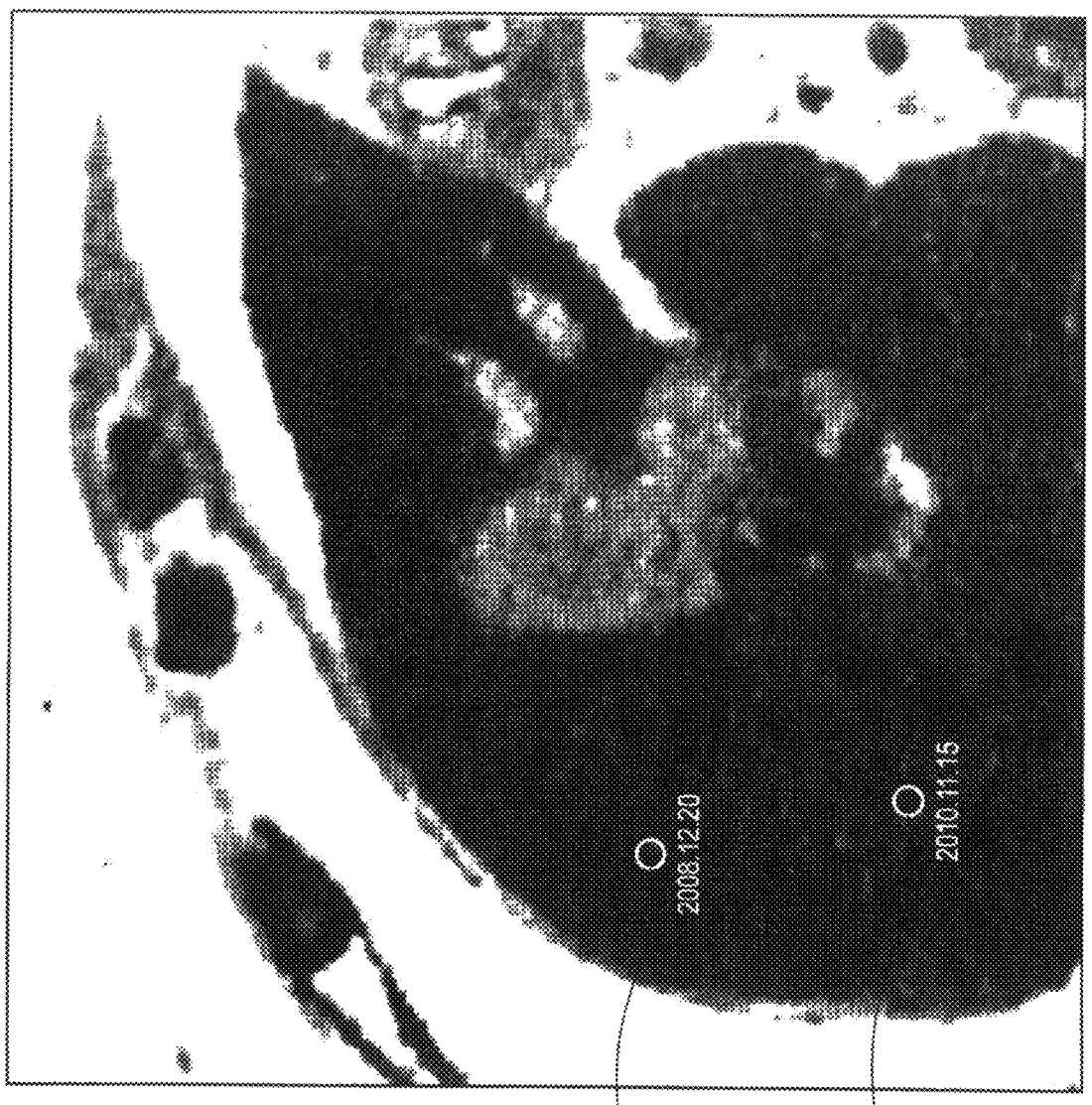
FIG. 4 is a view showing an example of an MPR image which is posteriorly generated and displayed and to which paracentesis information is added.

FIG. 4 is a view showing an example of a CT image which is posteriorly generated and displayed and to which paracentesis information is added. As shown in FIG. 4, dates, biopsy results, and the like are displayed at corresponding positions on a desired CT image, together with a needle tip position in each paracentesis executed in the past. In addition, the observer can simultaneously display the CT image to which the paracentesis information shown in FIG. 4 is added and an ultrasonic image (including the needle tip positions) (and needle tip positions and the like added to the ultrasonic image) associated with the CT image. Note that dates, biopsy results, and the like may be displayed stepwise by selecting desired needle tip positions on a CT image and an ultrasonic image with the mouse or the like.

An observer such as a doctor can posteriorly add and update the contents of paracentesis information corresponding to paracentesis at a desired date by inputting a biopsy result and the like from the input device 13 while observing the CT image displayed as shown in FIG. 4. In addition, needle tip positions (or regions corresponding to the needle tip positions) may be displayed in different colors or the shape of a marker assigned to each position may be changed in accordance with examination results or examination dates in the following manner. If, for example, a biopsy result is positive, the needle tip position is displayed in red (or in a rectangular shape). If a biopsy is negative, the needle tip position is displayed in blue (or in a circular shape). Furthermore, for example, in the case shown in FIG. 4, pieces of paracentesis information corresponding to a plurality of paracenteses are displayed. However, it is possible to display only desired paracentesis information or hide unnecessary paracentesis information, as needed. Paracentesis information may be stored for each trigger event or each group of trigger events, which is, for example, a group of a plurality of trigger events occurring in a day.

(Second Application)

In step S2, it is possible to use a CT image including needle tip positions in past paracentesis as a monitoring image by performing association (calibration) between paracentesis information added volume data generated in the past and the current scanning cross-section position and needle tip position. According to this arrangement, it is possible to display a CT image corresponding to the current scanning cross-section together with an ultrasonic image acquired in real time and simultaneously display paracentesis information including a needle tip position and the like in the past paracentesis. In this case, the current needle tip position and the past needle tip position are preferably displayed in different colors or different shapes.

The arrangement according to this application allows detailed suitable review of a past puncture result when performing puncture again. In addition, it is possible to execute current paracentesis while seeing a past puncture result and suitably support double ablation such as RFA, systematic biopsy for prostate cancer, and the like.

(Third Application)

New paracentesis information added volume data can be generated by copying the paracentesis information of paracentesis information added volume data onto another volume data.

For example, the control processor 31 performs relative alignment (calibration) between paracentesis information added volume data and another volume data (to which paracentesis information may be added or not). The paracentesis information generation unit 35 generates new paracentesis information by rewriting the position information included in the paracentesis information into the coordinate system of another volume data. The paracentesis information added data generation unit 37 generates new paracentesis information added volume data by adding the new paracentesis information to another volume data. If another paracentesis information is added to another volume data, the new paracentesis information is added to another volume data while the other paracentesis information is left unchanged (separately from the other paracentesis information).

Using the arrangement according to this application makes it possible to copy paracentesis information between, for example, volumes acquired by different modalities (e.g., CT volume data and ultrasonic volume data), volumes acquired by different imaging modes (e.g., contrast-enhanced volume data and non-contrast-enhanced volume data), or volume data before and after a treatment. This makes it possible to recognize a needle tip position or the like by using a plurality of images acquired by a plurality of modalities or a needle tip position or the like by using a plurality of images corresponding to periods before and after a treatment or the injection of a contrast medium.

(Fourth Application)

The direction and moving velocity of the puncture needle may be calculated from a temporal change in the needle tip position detected by the puncture needle position sensor 42 and may be displayed in a predetermined form together with paracentesis information and a CT image to which the paracentesis information is added. In this case, the moving velocity may be a numerical value or may be displayed stepwise in predetermined forms, for example, "0", "low", "intermediate", and "high". Obviously, the calculated direction and moving velocity of the needle tip position can be included in paracentesis information. In addition, it is possible to use, as a trigger event in step S4, the timing at which the moving velocity of the needle tip position exceeds a predetermined threshold, the timing at which the moving direction is changed, a combination of them, or the like. When a temporal change in needle tip position is to be stored as a trigger event, the movement of the needle tip position may be displayed as a moving image on a CT image. This makes it possible to reproduce at how much moving velocity the puncture needle was operated from a specific direction.

The arrangement according to this application needs to fix the needle tip for a few minutes in, for example, the case of an RFA treatment, but can visually provide, in real time, support information for determining whether the needle tip is being held, by displaying velocity information.

(Fifth Application)

The puncture needle position sensor 42 is attached to the tip of the puncture needle or sometimes to the proximal end of the puncture needle. In the latter case, a needle tip position is preferably calculated in consideration of how much the puncture needle is curved (posture and curved state). This application is configured to execute the above paracentesis support processing in consideration of how much the puncture needle is curved.

The paracentesis information generation unit 35 corrects the current needle tip position of the puncture needle based on at least one of the needle tip position received from the puncture needle position sensor 42 and the shape, posture, and position of the puncture needle on the current ultrasonic image, and generates paracentesis information by using the needle tip position after the correction. With this arrangement, the volume data to which the paracentesis information reflecting the needle tip position after the correction is added and the ultrasonic image to which the needle tip position after the correction is added are stored.

(Effects)

The ultrasonic diagnostic apparatus described above can store paracentesis information including the needle tip position of the puncture needle at a desired timing during paracentesis, with the paracentesis information being added to volume data corresponding to a CT image used for monitoring in the paracentesis, while storing an ultrasonic image used for monitoring in the paracentesis, with the needle tip position being added to it. In addition, it is possible to individually add paracentesis information including a needle tip position and the like to the same volume data at each of different times in the same paracentesis. Furthermore, it is possible to individually add paracentesis information including a needle tip position and the like to the same volume data for each of different paracenteses. The observer can simultaneously differentiate and visually recognize a plurality of puncture portions by using volume data in a range wider than that of ultrasonic waves. It is therefore possible to easily and quickly implement review of paracentesis with high objectivity, while reducing the operation load on the observer. In addition, it is possible to provide an evidence with high objectivity concerning paracentesis.

In addition, it is possible to perform current paracentesis while visually recognizing a past paracentesis result on a monitoring image by using paracentesis information added volume data generated in the past for monitoring in the current paracentesis. This can support the operator in paracentesis, and hence can improve the efficiency of a puncture treatment and the quality of paracentesis.

The above arrangement can also achieve the same effects as those of the first embodiment.

Note that the present invention is not directly limited to the above embodiment, and constituent elements can be modified and embodied in the execution stage within the spirit and scope of the invention. For example, the following are concrete modifications.

(1) Each function associated with this embodiment can also be implemented by installing programs for executing the corresponding processing in a computer such as a workstation and loading them in a memory. In this case, the programs which can cause the computer to execute the corresponding techniques can be distributed by being stored in recording media such as magnetic disks (Floppy® disks, hard disks, and the like), optical disks (CD-ROMs, DVDs, and the like), and semiconductor memories.

(2) The above embodiment is configured to store paracentesis information while adding it to volume data. However, the storage form of paracentesis information is not limited to this. For example, paracentesis information and volume data may be managed as different files which are associated with each other.

(3) The above embodiment has exemplified the case in which a puncture needle position is detected by using magnetism. However, the present invention is not limited to this. For example, a needle tip position may be detected by an optical scheme. In addition, the present invention is not limited to a case in which a position sensor is used, and a needle tip position may be detected by using an image recognition technique.

Figure 5:
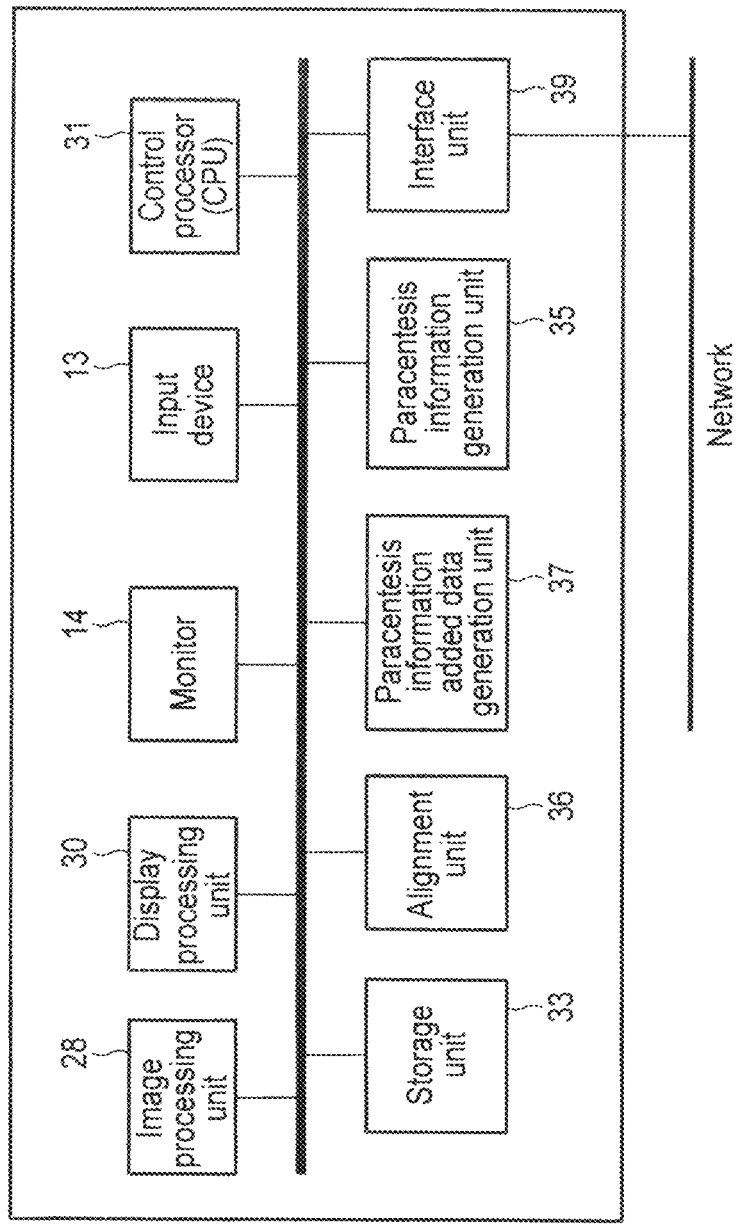
FIG. 5 is a block diagram showing the arrangement of a medical image processing apparatus according to the embodiment.

(4) The above embodiment has exemplified the case in which the paracentesis support function is implemented by using the ultrasonic diagnostic apparatus. However, the present invention is not limited to this, and the paracentesis support function may be implemented by using other modalities (medical image diagnostic apparatuses such as an X-ray computed tomography apparatus, magnetic resonance imaging apparatus, and X-ray diagnostic apparatus). In addition, the generation of paracentesis information, the generation of paracentesis information added volume data, the reproduction of paracentesis information added volume data, copying between the volume data of paracentesis information, and the like may be implemented by a medical image processing apparatus typified by a workstation like that shown in FIG. 5. In this case, it is possible to implement the generation of puncture information by acquiring the position of a medical tool with respect to an imaging region from a medical image diagnostic apparatus used for monitoring a medical tool such as a puncture needle in an object.

(5) The above embodiment has exemplified the case in which paracentesis is performed. However, the present invention is not limited to this. For example, the support function according to this embodiment can be applied to operations using other medical tools (a catheter and the like).

(6) Each of the function of the described embodiments may be implemented by one or more processing circuits. A processing circuit includes a programmed processor, as a processor includes circuitry. A processor circuit also includes devices such as an application specific integrated circuit (ASIC) and conventional circuit components arranged to perform the recited functions.

Note that the present invention is not directly limited to the above embodiment, and constituent elements can be modified and embodied in the execution stage within the spirit and scope of the invention. In addition, various inventions can be formed by proper combinations of a plurality of constituent elements disclosed in the above embodiments. For example, several constituent elements may be omitted from all the constituent elements disclosed in the above embodiments. Furthermore, constituent elements in the different embodiments may be combined, as needed.

The invention claimed is:

1. An ultrasonic diagnostic apparatus comprising:
an ultrasonic probe that scans an object; and
processing circuitry:
that obtains a first medical image by scanning a first imaging region in the object with the ultrasonic probe at a first date, the first imaging region including a tip of a first needle;
that acquires a position of the tip of the first needle in real time;
that acquires volume data corresponding to a three-dimensional region including the first imaging region;
that decides a first positional relationship between the volume data and the first imaging region;
that decides a position of the tip of the first needle with respect to the volume data based on the position of the tip of the first needle and the first positional relationship;
that generates support volume data by adding first support information to the volume data according to a first event including a first instruction to the processing circuitry, the first support information including the first date and the position of the tip of the first needle with respect to the volume data;
that obtains a second medical image by scanning a second imaging region in the object with the ultrasonic probe at a second date, the second imaging region including a tip of a second needle;
that acquires a position of the tip of the second needle in real time;
that decides a second positional relationship between the support volume data and the second imaging region;
that decides a position of the tip of the second needle with respect to the support volume data based on the position of the tip of the second needle and the second positional relationship,
that updates the support volume data by adding second support information with maintaining the first support information, according to a second event including a second instruction to the processing circuitry, the second support information including the second date and the position of the tip of the second needle with respect to the support volume data; and
that controls to simultaneously display an image of the object, a first marker, a second marker, the first date, and the second date based on the updated support volume data, wherein the first marker and the second marker are displayed in the image and respectively represent positions of tips of the first needle and the second needle, and the first date and the second date are respectively displayed near the first marker and the second marker, wherein
the first support information and the second support information are added to volume data corresponding to a CT image used for monitoring in the paracentesis, while the position of the tip of the first needle and the position of the tip of the second needle are added to an ultrasonic image used for monitoring in the paracentesis.

2. The apparatus of claim 1, further comprising a storage that stores the support volume data.

3. The apparatus of claim 1, wherein the processing circuitry detects occurrence of predetermined events concerning operations of the first needle and the second needle, wherein the processing circuitry calculates each position of the first needle and the second needle corresponding to points of occurrence of the events with respect to the volume data in response to the occurrence of the predetermined events, and generates the first support information including the calculated position of the first needle, and generates the second support information including the calculated position of the second needle.

4. The apparatus of claim 1, wherein the processing circuitry generates a second medical image by adding a position of the needle in the imaging region to the medical image corresponding to a time of occurrence of the predetermined event, and stores the second medical image ultrasonic image in association with the support volume data.

5. The apparatus of claim 1, wherein the first support information and second support information includes at least one of an operator who operates the first needle and the second needle, a thickness of the first needle and the second needle, a time when the predetermined event has occurred, a result of examination using the first needle and the second needle, and a finding from a doctor, respectively.

6. The apparatus of claim 1, wherein the processing circuitry uses, as the predetermined events, at least one of a store instruction for support volume data input at a desired timing, a freeze display instruction for a medical image, a cauterization start operation, a tissue collection start operation, a moving velocity of the first needle and the second needle, a change in moving direction of the first needle and the second needle, an elapse of a predetermined time from a time point at which an operator pressed a switch, and detection of standstill of the first needle and the second needle in a tissue over a predetermined time.

7. The apparatus of claim 1, wherein the first support information further includes at least one of a direction of the first needle and a moving velocity of the first needle, and the second support information further includes at least one of a direction of the second needle and a moving velocity of the second needle.

8. The apparatus of claim 1, wherein the processing circuitry:
executes alignment with the imaging region by using past support volume data to which the first support information is added the volume data obtained in advance;
generates a support image corresponding to the second imaging region by using the past support volume data after the alignment;
displays, on a monitor, the first support information which is added to the past support volume data, the support image, and a medical image corresponding to the second imaging region.

9. The apparatus of claim 1, wherein the processing circuitry:
executes alignment between first volume data to which the first support information is added and second volume data, and
generates new support volume data by adding the first support information added to the first volume data to the second volume data.

10. The apparatus of claim 1, wherein the processing circuitry:
calculates at least one of a moving velocity and a moving direction of each of the first needle and the second needle,
generates the first support information including at least one of the calculated moving velocity and moving direction, and generates the second support information including at least one of the calculated moving velocity and moving direction.

11. The apparatus of claim 1, wherein the processing circuitry:
corrects a position of the second needle on the volume data based on a curved state of the first needle, and
generates the second support information based on the position after the correction.

12. The apparatus of claim 1, wherein the first support information and the second support information are generated each time the one of predetermined events occurs.

13. The apparatus of claim 1, wherein the processing circuitry selectively displays the at least one part of the first support information and the second support information.

* * * * *